United States Patent [19]

Hayashi

[11] Patent Number: 5,416,540

[45] Date of Patent: May 16, 1995

[54] APPARATUS FOR VISUAL ACUITY TEST

[75] Inventor: Akihiro Hayashi, Toyokawa, Japan

[73] Assignee: Nidek Co., Ltd., Japan

[21] Appl. No.: 188,834

[22] Filed: Jan. 31, 1994

[30] Foreign Application Priority Data

Feb. 4, 1993 [JP] Japan .................................. 5-041970

[51] Int. Cl.$^6$ .............................................. A61B 3/02
[52] U.S. Cl. .................... 351/239; 351/243
[58] Field of Search ............... 351/243, 239, 241, 242

[56] References Cited

U.S. PATENT DOCUMENTS 4,550,990 11/1985 Trispel et al. ...................... 351/243
5,129,720 7/1992 Jovicevic ............................ 351/243

FOREIGN PATENT DOCUMENTS 59-19107 2/1984 Japan .
61-132629 6/1988 Japan .

Primary Examiner—William L. Sikes
Assistant Examiner—Hugn Xuan Dang
Attorney, Agent, or Firm—Parkhurst, Wendel & Rossi

[57] ABSTRACT

An apparatus for visual acuity testing by presenting visual test charts to an examinee by utilizing an electro-optic effect, the apparatus comprising a test charts displaying device in which test charts of a same kind are arranged in each chart line per visual acuity value and constitute a plurality of test chart lines, and test charts in different kind of test chart line individually arranged in a space between test charts in at least a test chart line, and a kind of test charts to be displayed on the test chart displaying device is selected by a selecting device.

12 Claims, 12 Drawing Sheets

APPARATUS FOR VISUAL ACUITY TEST

BACKGROUND OF THE INVENTION

1. Field of the Invention

The present invention relates to an apparatus for visual acuity test, in particular to an apparatus for visual acuity test provided with plural kinds of test charts, for instance, Landolt ring charts, character chart and others.

2. Description of Related Art

In conventional apparatuses for testing visual acuity of an examinee's eye by presenting test charts to the examinee, there is known an apparatus utilizing a method in which the test charts, being printed on semitransparent plates and others, are illuminated one by one from the back of the semitransparent plate by a lamp and the like so that a test chart to be read by the examinee is identified. In such an apparatus for visual acuity testing, the test charts are individually presented to the examinee as above, and besides, a plurality of test charts each for the different visual acuity value or test charts for the same visual acuity value can be synchronously presented. Consequently, the time for testing visual acuity can be shortened.

In addition, there is also an apparatus for visual acuity test in which different kinds of test charts can be utilized by exchanging test chart plates, for instance, from a test chart plate provided with Landolt rings thereon to another test chart plate provided with character charts thereon.

Another apparatus for testing visual acuity has been also proposed in Japanese Laid-Open Utility Model No. SHO 59-19107, in which visual test charts are presented to the examinee by utilizing an electro-optical effect such as liquid crystal and the like.

However, in the former apparatus in which test charts are illuminated from the back of the semitransparent plate by a lamp, presenting various kinds of test charts, such as Landolt rings and character test charts and others, one needs to exchange test chart plates according to the sort of test chart to be used. However, it is troublesome and difficult to exchange test chart plates in testing the visual acuity of an examinee's eye.

In the latter kind of testing apparatus utilizing the liquid crystal, there is not practicable apparatus ensuring the standard testing distance between the apparatus and the examinee; 3 meter (m) or 5 meter (m). The reason is that, in order to display various test charts for a testing distance of 5 m on a liquid crystal plate at actual distance, it is necessary to have a large liquid crystal display area and therefore such apparatus can not be actualized economically and technically.

SUMMARY OF THE INVENTION

The present invention has been made in view of the above circumstances and aims to overcome the above problems and to provide an apparatus for visual acuity test in which test charts can be promptly switched by utilizing an electro-optic effect, and also which is compact and at low cost.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an apparatus for testing visual acuity of this invention, which is for presenting visual test charts to examinee by utilizing an electro-optic effect, comprises a test charts displaying means in which test charts of a same kind are arranged in each chart line per visual acuity value and constitute a plurality of test chart lines, and test charts in different test chart line individually arranged in a space between test charts in at least a test chart line, and a selecting means for selecting a kind of test charts to be displayed on said test charts displaying means.

In another aspect of the present invention, an apparatus for testing visual acuity, which is for presenting test charts for visual acuity test to examinee by utilizing electro-optic effect, comprises a test chart displaying means, on which test chart lines each consisted of test charts for the same visual acuity value are classified into plural groups based on the predetermined reference, and test chart lines of one group are alternately arranged between test chart lines of a different group, and a selecting means for selecting one of test chart line groups to be displayed on said second displaying means.

In third aspect of the present invention, an apparatus for visual acuity test, which is for presenting test charts for visual acuity test to examinee by utilizing electro-optic effect, comprises a displaying means provided with plural Landolt ring charts within a visual field for test, each of Landolt ring charts being consisting of a plurality of liquid crystal elements and forming a ring shape, and a selecting means for selecting whether slit directions of Landolt ring charts to be displayed on said third displaying means are only up and down, right and left directions, or further include oblique directions.

According to the present invention, it is possible to provide electro-optical displaying means practicable for visual acuity testing apparatus because of constituting test charts with element utilizing electro-optic effect, for instance, liquid crystal and the like, and also arranging such test charts efficiently. Such apparatus can have, accordingly, displaying system to be promptly conducted by switching operation, which has not been provided for conventional visual acuity testing apparatuses.

Generally, the cost of a liquid crystal plate increases as the displaying area of the plate enlarges. In the present invention, however, by efficiently arranging test charts for high visual acuity value and the same for low visual acuity value, a liquid crystal plate may not need a large area, so that an economical effect can be also improved. Convenience of visual acuity testing apparatus can be further increased by using Landolt ring test charts and numeral test charts in effective combination.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of one preferred embodiment of an apparatus for visual acuity test embodying the present invention will now be given referring to the accompanying drawings.

Figure 1:
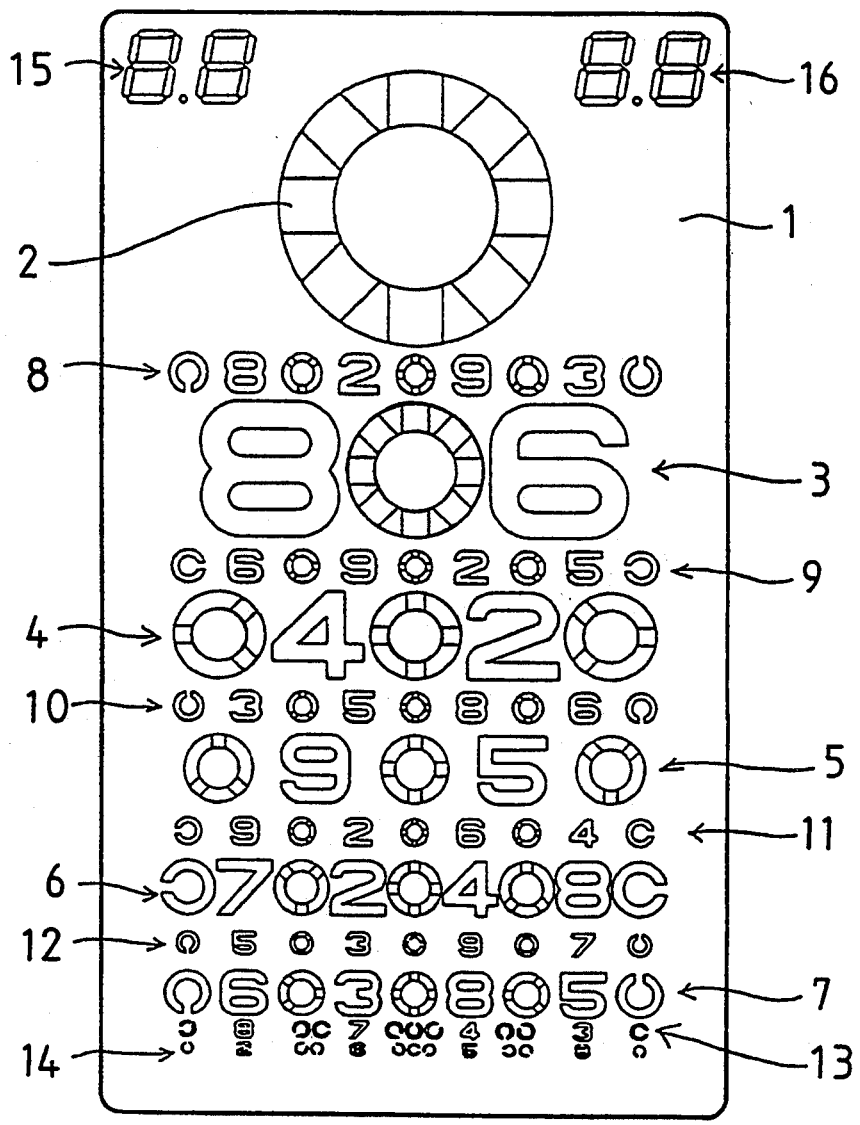
FIG. 1 is a diagram of showing an arrangement of test charts of an apparatus for visual acuity test in an embodiment according to the present invention.

In FIG. 1, shown is an arrangement of visual test charts provided for the testing apparatus in the embodiment.

A liquid crystal plate 1 is provided with polarizing plates at the back and forward sides respectively, polarized axes of which intersect at right angles with each other, and also a lighting device (not shown) is disposed at the back side of the liquid crystal plate 1, for instance, a fluorescent lamp. Crystalline liquid display utilized in the present embodiment is applied with what is called twisted nematic (TN) system utilizing property that, when voltage is applied to each element provided in the liquid crystal plate, each molecular axis of liquid crystal in each element will be brought into disposition along a direction of electric field and thereby light beam is cut off in passing through two polarizing plates. A segment type is used as the displaying element for test charts and others in the present embodiment, a segment type is used. Another system for displaying by liquid crystal may be also utilized in the present invention.

In the liquid crystal plate 1, as shown in FIG. 1, a Landolt ring chart 2 and test chart lines 3–14 are arranged. The Landolt ring chart 2 is 72.7 mm in outer diameter (visual angle of slit 10' if seen at a distance of 5 m) and for the visual acuity value 0.1. When voltage is applied to all elements of ring excepting an element in one of eight directions, the Landolt ring chart 2 can therefore present a test chart of eight sorts of test charts for visual acuity value 0.1, each of which has a slit in a different direction.

In the test chart line 3, a Landolt ring chart for visual acuity value 0.2 is disposed at a center thereof. At respective center in test chart lines 4–7, Landolt ring charts of visual acuity value 0.3, 0.4, 0.5 and 0.6 are respectively arranged, each of which is disposed at intervals of more than 15 mm so as to be recognized individually while synchronously presented. There are, in a horizontal direction, three Landolt ring charts in the test chart lines 4 and 5 respectively, five in the test chart lines 6 and 7 respectively at intervals so as to be easily recognized at the time of synchronously display. It is sufficient even if slits in eight directions per one visual acuity value can be presented to an examinee, therefore, each Landolt ring chart in the test chart lines 4–7 need not be provided with eight slits individually. Consequently, when the slit directions are varied mutually in three kinds of Landolt ring charts, as shown in FIG. 1, each of which has four slits, three slits or one slit, liquid crystal elements can be reduced.

Test chart lines 8, 9, 10, 11 and 12 are provided with test charts for visual acuity value 0.7, 0.8, 0.9, 1.0 and 1.2 respectively, and the test chart lines 8–12 are sequentially arranged between the test chart lines 2, 3, 4, 5, 6 and 7. Each Landolt ring chart for visual acuity value 0.7 in the test chart line 8 is 10.39 mm in outer diameter and the visual angle of slit is 1.4' if seen at a distance of 5 m, it can be accordingly disposed in a space of 15 mm without overlapping on another test chart line.

In the test chart lines 13 and 14, small test charts for visual acuity value 1.5 and 2.0 are arranged respectively, it is accordingly possible to simplify manufacturing of the apparatus by providing a plurality of Landolt ring charts each having only one slit as shown in FIG. 1. The apparatus in the above embodiment is designed so as to leave a space of more than 15 mm between the edge of the liquid crystal plate 1 and each test chart disposed at outermost sides in each of test chart lines 3–14.

Further to Landolt ring charts, numeral test charts are also arranged in the test chart lines 3–14 of the apparatus for visual acuity test in the embodiment. Numeral test charts "8" and "6" are respectively arranged at both sides of a Landolt ring chart in the test chart line 3. Similarly, the test chart lines 4–14 are provided with two through four numeral test charts respectively. Namely, each space between two test charts of same kind is left by a space corresponding with at least one test chart.

In the liquid crystal plate 1, numeral 15 is a digital display portion to indicate the lowest visual acuity value of displayed test charts and numeral 16 is a digital display portion to indicate the highest visual acuity value of the same. If only one test chart is displayed, the digital display portion 16 indicates the visual acuity value thereof.

Figure 2:
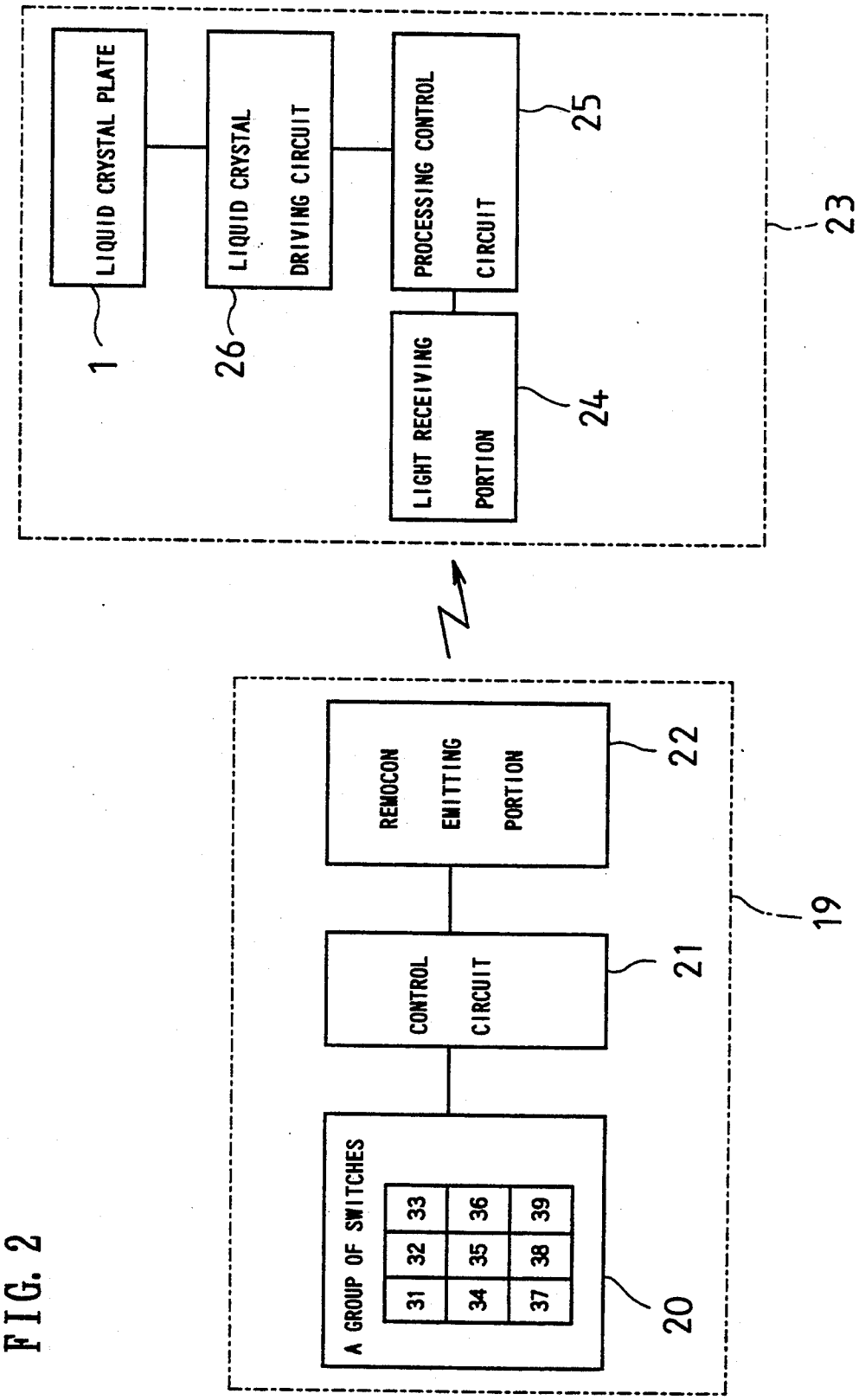
FIG. 2 is a block diagram to explain the construction of the apparatus according to the present invention.

FIG. 2 shows a block diagram to explain the construction of the apparatus for visual acuity test in the present embodiment.

A remote controller 19 to operate the apparatus unit 23 by pulse signal is provided with a group of switches 20, a control circuit 21 and a remocon emitting portion 22 which is consisted of code modulating circuit, output buffer and emitting element. The group of switches 20 includes a switch 31 for selecting Landolt ring test chart group, a switch 32 for selecting numeral test chart group, a slit selecting switch 33 for selecting that a slit of each Landolt ring chart is displayed only in one of up and down, right and left directions when displaying Landolt ring chart group is selected, a slit selecting switch 34 for selecting that a slit of each Landolt ring chart is provided in one of eight directions including oblique directions, a display mode selecting switch 35 for synchronously displaying visual test charts disposed in a same vertical line, a switch 36 to select a test chart group for low visual acuity value, a switch 37 to select a test chart group for high visual acuity value, a selecting switch 38 for synchronously displaying test charts in a horizontal line, and a batch displaying switch 39.

A signal generated by a group of switches 20 is transmitted through the control circuit 21 to the remocon emitting portion 22, and converted to an infrared pulse signal to be transmitted to the apparatus unit 23. The infrared pulse signal emitted by the remocon emitting portion 22 is taken through a light receiving window of the apparatus unit 23 and converted to a digital signal at a light receiving portion 24 consisted of light receiving element, pre-amplifier and wave detecting circuit. The digital signal is then input to a processing control circuit 25. The processing control circuit 25 controls through a liquid crystal driving circuit 26 the liquid crystal plate 1, and thus displays designated test charts and visual acuity values thereon.

Operation of the apparatus constructed as described above will be explained.

In the apparatus for visual acuity test according to the present invention, based on operating the group of switches 20, test charts to be displayed can be selected as described below. By combining these selections of test charts to be displayed, the desired visual acuity test can be exactly conducted.

The first selection is of the kind of test chart to be displayed, namely, either Landolt ring chart or numeral test chart is selected by the Landolt ring chart displaying switch 31 or the numeral test chart displaying switch 32. Once selected, it is not necessary to designate a kind of test chart after every change of individual test charts to be displayed, unless another kind of test chart is selected by switching operation.

The second selection is, in a case where a group of Landolt ring test chart is selected at the above first selection, of whether the group of Landolt ring test chart include Landolt ring test charts each of which has a slit in an oblique direction. As for selection of whether visual acuity test with Landolt ring charts each having a slit only in one of up and down, right and left directions, or visual acuity test with Landolt ring charts having also a slit in oblique direction, this depends on the examiner's way and also a primary factor such as examinee's age and testing time and others, and either test is conducted by only the slit selecting switch 34 or both the same and the slit selecting switch 33.

Figure 3:
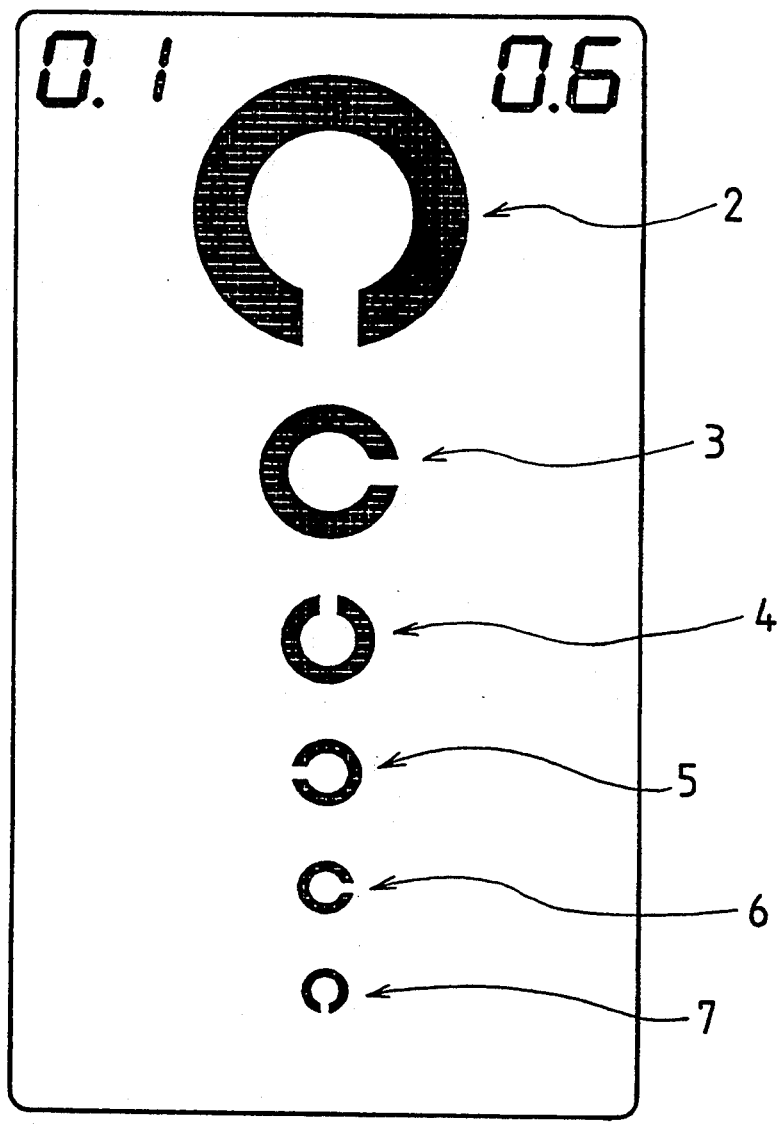
FIG. 3 is a diagram of an example of synchronously displaying Landolt ring charts disposed at a center in each test chart line, which are visual acuity values 0.1–0.6 respectively.

The third is of selecting a display mode to display test charts in a vertical line in order to promptly examine the examinee's approximate visual acuity value. FIG. 3 shows a display situation in a case where Landolt ring chart group is selected at the first selection, and test with Landolt ring chart each having a slit in one of up and down, right and left directions is selected at the second selection, and further displaying Landolt ring charts in a vertical line and for low visual acuity value are selected by the mode selecting switch 35 and the low visual acuity value group selecting switch 36 respectively. Thus, Landolt ring charts each positioned at a center in each of test chart lines 2 through 7 are synchronously displayed, so that the examinee may be made to read one by one each slit direction of Landolt ring charts for visual acuity values 0.1-0.6.

Figure 4:
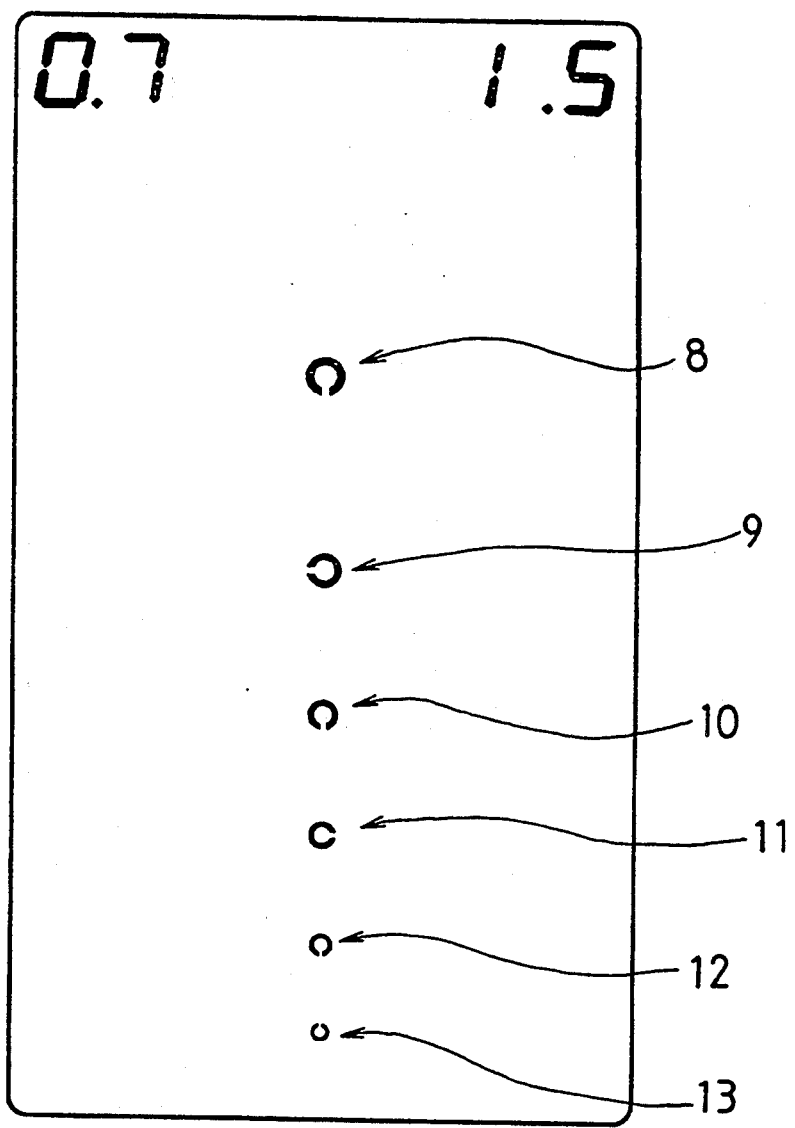
FIG. 4 is a diagram of an example of synchronously displaying, as same as in FIG. 3, Landolt ring charts each of which are for visual acuity values 0.7–1.5 respectively.

On press of the switch 37 for selecting test chart group for high visual acuity value, the above display situation shown in FIG. 3 is changed to another display situation in which test charts for visual acuity values 0.7-1.5 are synchronously displayed as shown in FIG. 4.

Figure 5:
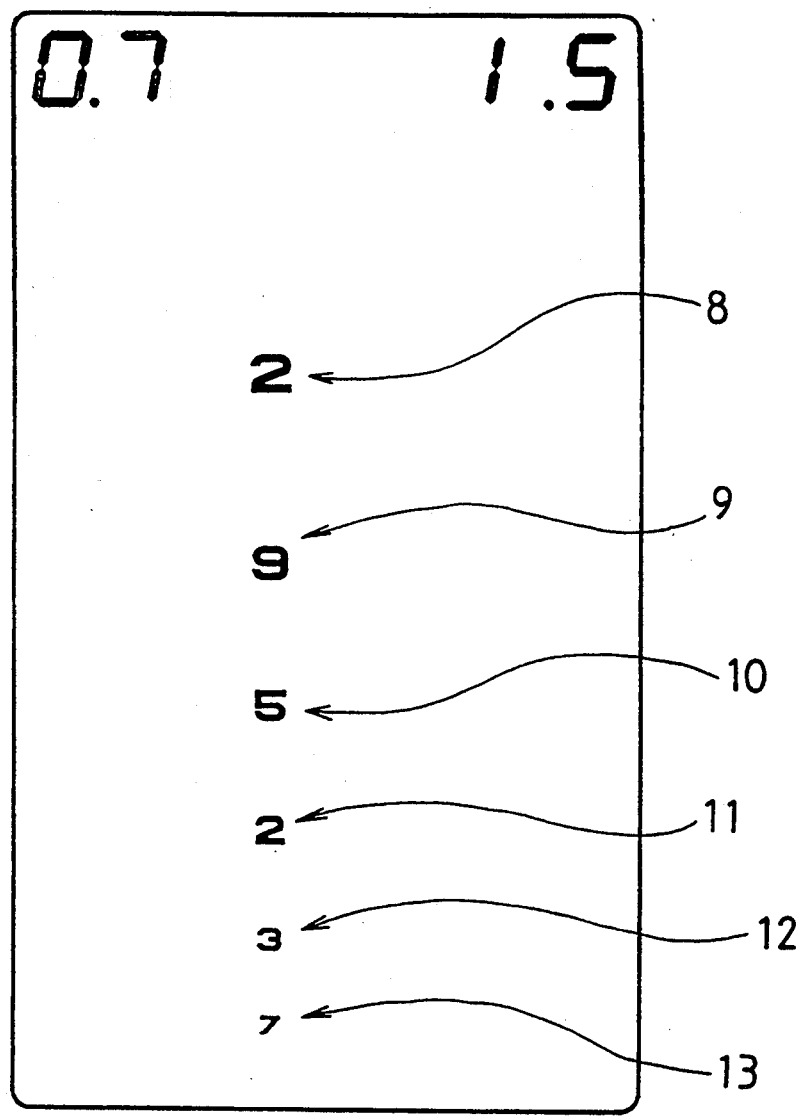
FIG. 5 is a diagram of an example of displaying numeral test charts in a vertical line.

FIG. 5 shows another display situation in a case where a numeral test chart group is selected instead of a Landolt ring test chart group at the first selection and, similarly in FIG. 4, test charts in a vertical line and for high visual acuity value are selected by pressing both the switch 35 and the switch 37.

Consequently, as described above, visual acuity test for visual acuity values 0.1-1.5 can be promptly conducted by using the mode displaying visual test charts in a vertical line.

Figure 6:
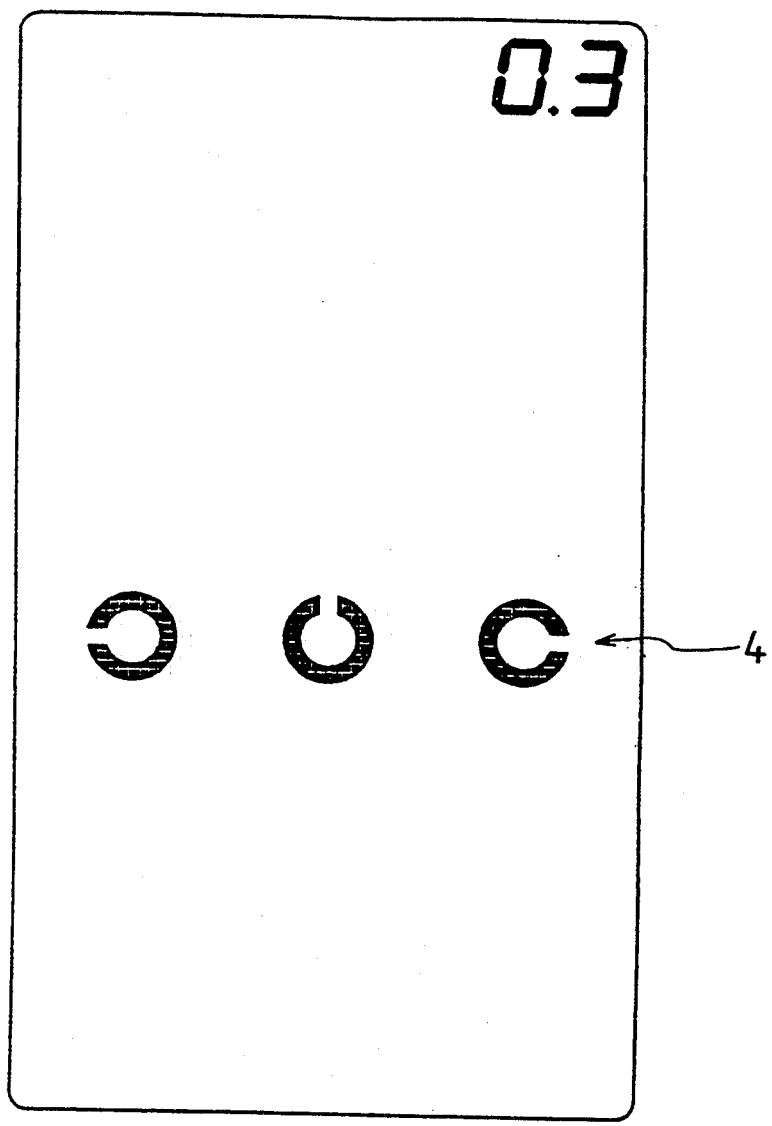
FIG. 6 is a diagram showing an example of selecting only Landolt ring charts each capable of having a slit in one of four directions, namely, vertical and horizontal directions, and designating the visual acuity value 0.3.
Figure 7:
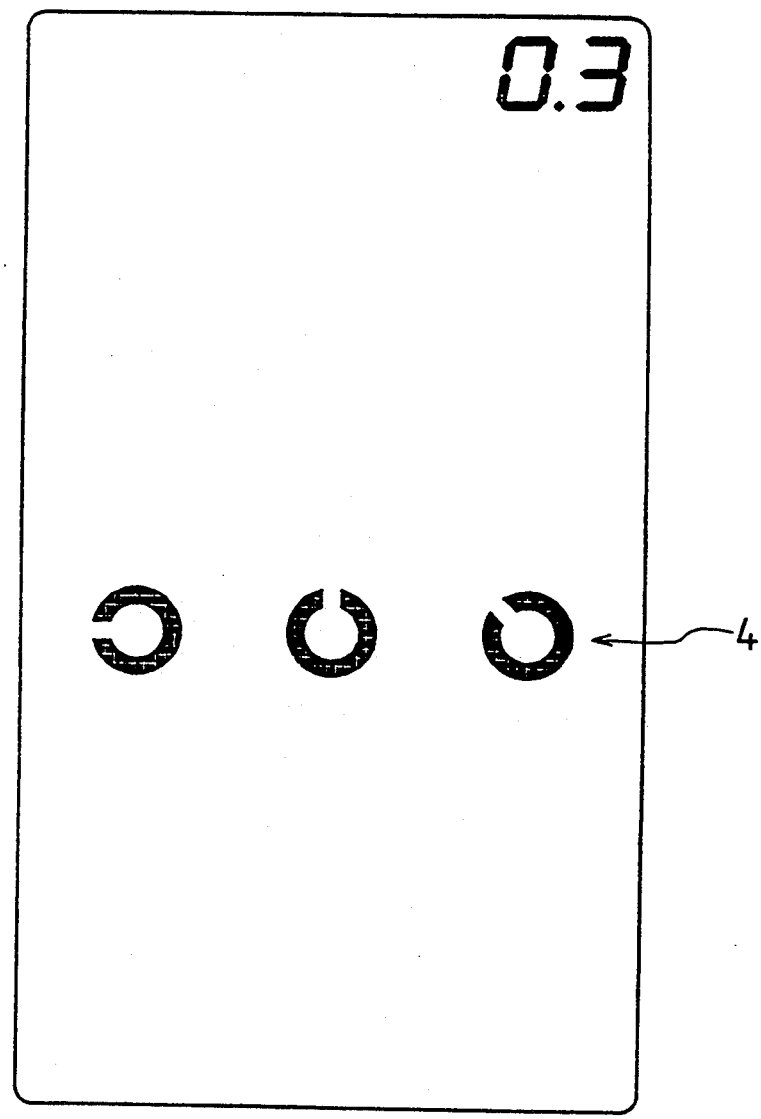
FIG. 7 is a diagram showing an example of selecting Landolt ring charts including further a slit in an oblique direction and designating the visual acuity value 0.3 at the same time.

The fourth selection is of selectively displaying a specified test chart line. In FIG. 6, shown is a display situation of when Landolt ring test charts each having a slit in one of up and down, right and left directions are selected at the first and second selections, further the visual acuity value 0.3 is designated by the test chart line selecting switch 38. In FIG. 7, shown is a display situation of when Landolt ring charts having further a slit in an oblique direction are also selected at the first and second selections and, similarly in FIG. 6, the visual acuity value 0.3 is designated.

Figure 8:
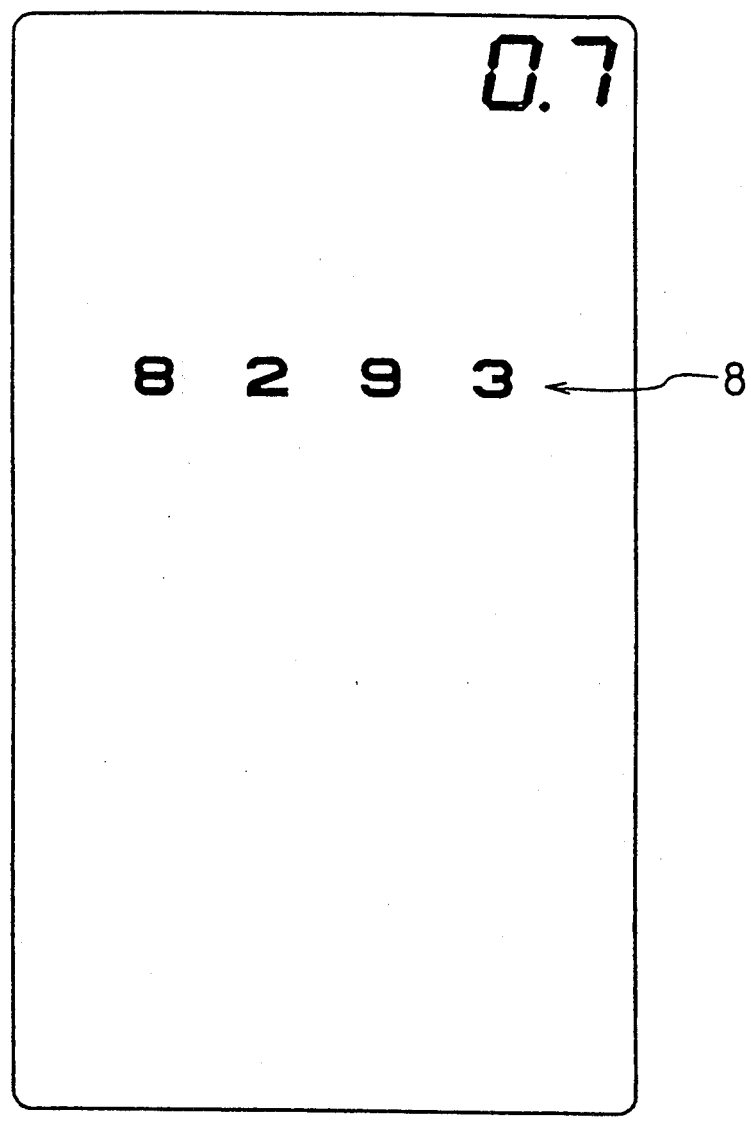
FIG. 8 is a diagram showing an example of selecting numeral test charts and designating the visual acuity value 0.7.

FIG. 8 shows a display example when a numeral test chart group is selected at the first selection and the visual acuity value 0.7 is designated by the switch 38.

As described above, by selectively displaying a specified test chart line, the apparatus for visual acuity test according to the present invention enables prompt test of whether the examinee has the designated visual acuity value or not.

Figure 9:
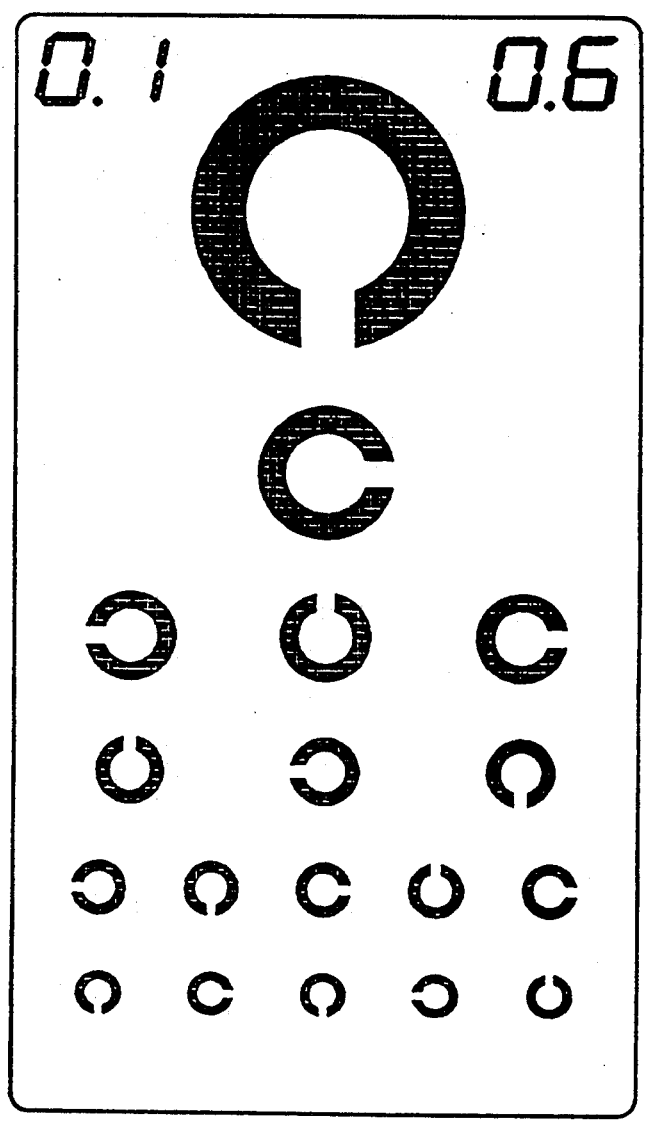
FIG. 9 is a diagram showing an example of selecting Landolt ring charts each capable of having a slit in one of four directions, vertical and horizontal directions and conducting batch display thereof.

The fifth selection is of batch display of same kind of test chart as similar as known printed test charts. In the present his embodiment, test charts are displayed in two classified sorts, one for visual acuity values 0.1-0.6 and another for visual acuity values 0.7-1.5 respectively. In FIG. 9, shown is a display example of when Landolt ring test charts having a slit in one of four directions; up and down, right and left, are selected and, the batch displaying switch 39 and the low visual acuity value group selecting switch 36 are both pressed, so that Landolt ring test charts each for one of visual acuity values 0.1-0.6 are displayed.

Figure 10:
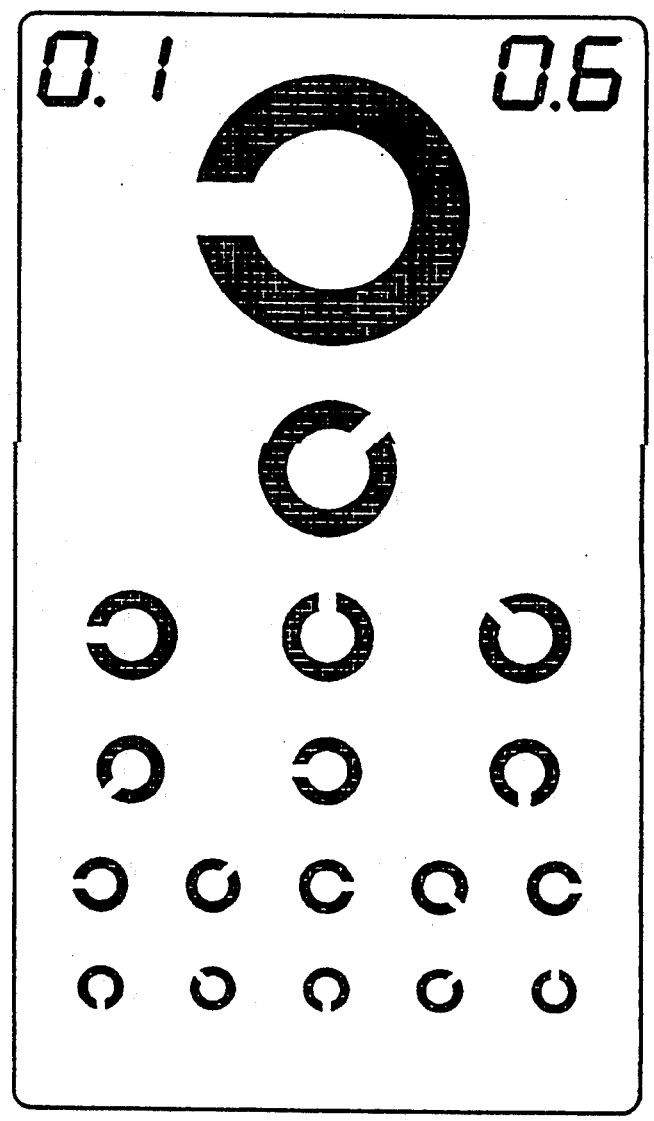
FIG. 10 is a diagram showing an example of displaying Landolt ring charts with a slit in oblique direction in addition to in FIG. 9.

FIG. 10 shows another example of Landolt ring test charts in FIG. 9 further including an oblique slit.

Figure 11:
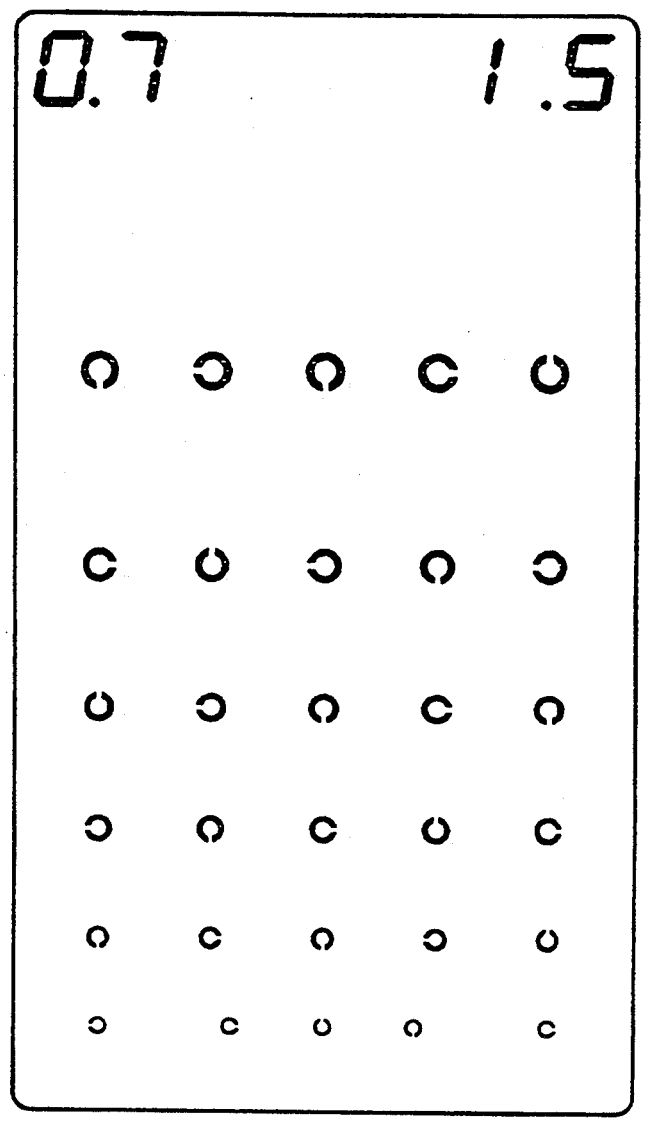
FIG. 11 is a diagram showing an example of displaying Landolt ring charts for high visual acuity value so that each chart has a slit in one direction of vertical and horizontal directions.

In FIG. 11, shown is a display example of when, instead of the above low visual acuity value group selecting switch 36, the high visual acuity value group selecting switch 37 is pressed, so that displayed are Landolt ring test charts for visual acuity values 0.7-1.5 each having a slit in one of four directions; up and down, right and left.

Figure 12:
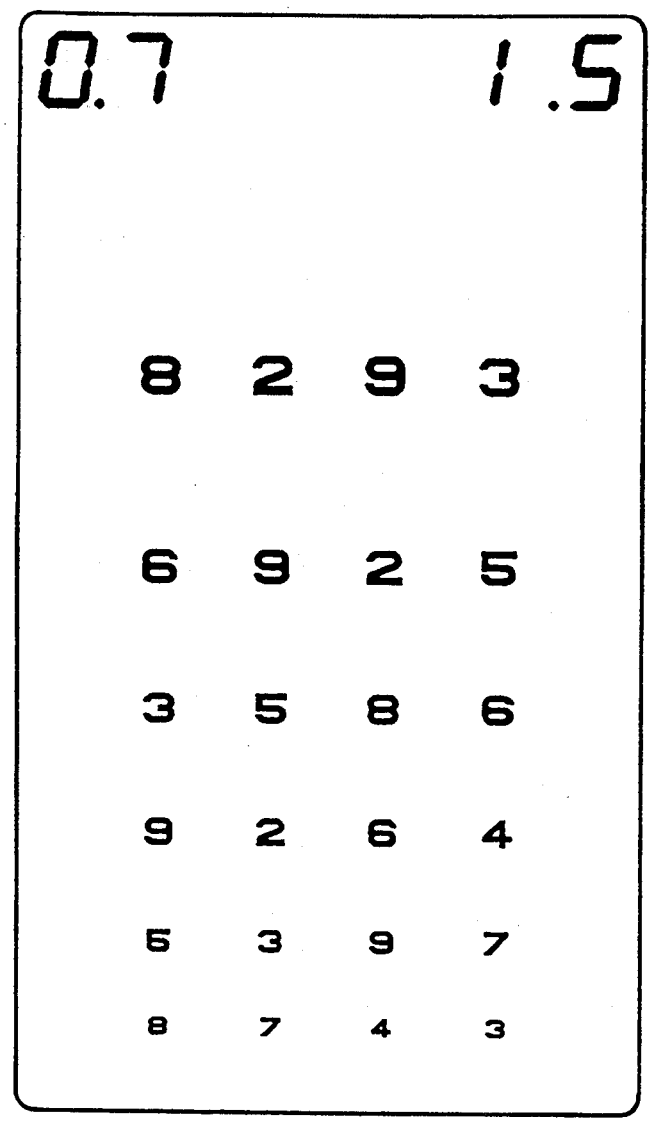
FIG. 12 is a diagram showing an example of synchronously displaying numeral test charts for high visual acuity value.

FIG. 12 shows a display example of when a numeral test chart group is selected by the switch 32 at the first selection and, the test chart group for high visual acuity value and batch display mode are selected by the switches 37 and 39 respectively.

The present invention may be embodied in other specific forms without departing from the spirit or essential characteristics thereof. For instance, in the above embodiment, although test charts having the same visual acuity value are arranged in a same test chart horizontal line, test charts having different visual acuity value may be arranged in a same line.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for testing visual acuity of an examinee, comprising:
    display means for electro-optically displaying test charts each comprised of at least one segment formed in a test chart figure, wherein test charts of the same visual acuity value are arranged in a line thereby to define a test chart line, said test charts forming a plurality of test chart lines which are divided into a plurality of groups including a first group and a second group, said first group comprising respective test chart lines arranged sequentially by visual acuity from a first visual acuity value to a second visual acuity value which is higher than said first visual acuity value, said second group comprising respective test line charts arranged sequentially by visual acuity from a third visual acuity value to a fourth visual acuity value, said third visual acuity value being higher than said second visual acuity value of said first group, wherein the test line charts of said second group are alternately disposed between the test line charts of said first group; and
    selecting means for selecting at least one test chart to be displayed by driving said display means.

2. The apparatus of claim 1, wherein each test chart line consists of test charts of the same visual acuity value and the same kind.

3. The apparatus of claim 1, wherein said at least one segment formed in a test chart figure is a liquid crystal segment.

4. The apparatus of claim 1, wherein said test charts comprise Landolt ring charts, and a plurality of said Landolt ring charts which have a relatively low visual acuity value each have a plurality of segments formed in a test chart figure for changing slit direction.

5. The apparatus of claim 1, wherein said selecting means is adapted to select test charts in a vertical line.

6. The apparatus of claim 1, wherein said selecting means is adapted to select one of said first and second groups.

7. The apparatus of claim 1, wherein said display means comprises a liquid crystal display plate on which said test charts are provided, said test chart lines including plural kinds of test charts, and wherein said selecting means comprises a remocon unit for selecting one kind of test charts of said plural kinds of test charts.

8. The apparatus of claim 7, wherein said plural kinds of test charts include Landolt ring charts.

9. The apparatus of claim 8, wherein at least one Landolt ring chart has a slit in an oblique direction, said remocon unit having means for optionally displaying said at least one Landolt ring chart when displaying said Landolt ring charts.

10. The apparatus of claim 8, wherein said remocon unit includes means for selecting test charts of a test chart line which is arranged horizontally.

11. The apparatus of claim 7, wherein said remocon unit includes means for selecting test charts in a vertical line.

12. The apparatus of claim 7, wherein said display plate includes means for displaying the visual acuity values of selected test charts.

* * * * *